US00PP23123P2

(12) United States Plant Patent
Zaiger et al.

(10) Patent No.: US PP23,123 P2
(45) Date of Patent: Oct. 23, 2012

(54) INTERSPECIFIC TREE NAMED 'KYLESE'

(50) Latin Name: ***Interspecific Prunus* species**
Varietal Denomination: Kylese

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 13/317,584

(22) Filed: Oct. 24, 2011

(51) Int. Cl.
*A01H 5/00* (2006.01)

(52) U.S. Cl. ..... Plt./180

(58) Field of Classification Search ..... Plt./180, Plt./185
See application file for complete search history.

*Primary Examiner* — June Hwu
*Assistant Examiner* — Louanne Krawczewicz Myers

(57) ABSTRACT

A new and distinct variety of interspecific tree, the fruit is characterized with the tree budded on 'Nemaguard' Rootstock (non-patented), grown on Handford sandy loam soil with Storie Index rating 95, in USDA Hardiness Zone 9, near Modesto, Calif. with Standard commercial fruit growing practices, such as pruning, thinning, spraying, irrigation and fertilization. Its novelty consist of the following combination of desirable features:

1. Fruit with an attractive orange skin color.
2. Fruit with good flavor and eating quality.
3. Regular and productive bearer of large size fruit.
4. Vigorous, upright tree growth.
5. Fruit with good handling and shipping quality.

1 Drawing Sheet

Botanical designation: Interspecific *Prunus* species.
Variety denomination: 'Kylese'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES: Among the existing varieties of apricots, plum and interspecifics, which are known to us and mentioned herein, 'Royal Zee' Plum (U.S. Plant Pat. No. 5,486), 'Flavor King' Interspecific (U.S. Plant Pat. No. 8,026), 'Tri-Gems' Apricot (U.S. Plant Pat. No. 6,755), 'PA7221-1' Apricot (U.S. Plant Pat. No. 7,035), 'Autumn Glory' Apricot (non-patented), 'Tracy' Apricot (U.S. Plant Pat. No. 3,062), 'Flaming Gold' Apricot (U.S. Plant Pat. No. 2,822) and the proprietary interspecifics '278LP84', '11M130' and '4G1180'.

STATEMENT REGARDING FEDERALLY SPONSORED RESEARCH AND DEVELOPMENT

Not applicable.

ORIGIN OF THE VARIETY: The new variety of interspecific tree, a combination of crosses between (*Prunus armeniaca* and *Prunus salicina*) was originated by us in our experimental orchard located near Modesto, Calif. from a cross between the selected proprietary seedlings with the field identification numbers '278LP84' and '11M130'. The seed parent (278LP84) originated from crossing the following varieties;

'Flaming Gold' Apricot (U.S. Plant Pat. No. 2,822), 'Royal Zee' Plum (U.S. Plant Pat. No. 5,486), 'PA7221-1' Apricot (U.S. Plant Pat. No. 7,035) and the proprietary plumcot '4G1180'. The pollen parent (11M130) originated from the crosses of the following varieties; 'Autumn Glory' Apricot (non-patented), 'Tracy' Apricot (U.S. Plant Pat. No. 3,062), 'Tri-Gems' Apricot (U.S. Plant Pat. No. 6,755) and 'Flavor King' Interspecific (U.S. Plant Pat. No. 8,026). A large number of these first generation seedlings were budded on established trees of 'Nemaguard' Rootstock (non-patented), to enhance earlier fruit production. Under close and careful observation the present budded seedling exhibited desirable fruit and tree characteristics and was selected in 2007 for additional asexual propagation and commercialization.

ASEXUAL REPRODUCTION OF THE VARIETY: Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY: The present new variety of interspecific tree [Apricot×(Plum×Plumcot)×Apricot×(Plum×Plumcot)] is of large size, vigorous upright growth and a productive and regular bearer of large size, orange flesh, freestone fruit with good flavor and eating quality. The fruit is further characterized by having an attractive orange skin color, being relatively uniform in size and maturity throughout the tree and having good handling, storage and shipping quality. In comparison to its seed parent (278LP84) the fruit of the new variety is larger in size and ripens approximately 10 days earlier. In comparison to its pollen parent (11M130) the tree produces a more consistent crop and the fruit ripens approximately 12 days earlier. In comparison to the commercial Interspecific variety 'Tasty Rich' (U.S. Plant Pat. No. 12,774) the fruit of the new variety is larger in size, has a darker orange skin and flesh color and ripens approximately 10 days later.

PHOTOGRAPH OF THE VARIETY: The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 6 year old tree and the colors are as nearly true as is reasonably possible in a color representation of this type.

DESCRIPTION OF THE VARIETY: The following is a detailed botanical description of the new variety of interspecific tree, its flowers, foliage and fruit, as based on observations of 6 year old specimens grown near Modesto, Calif., with color in accordance with Munsell Book of Color.

Tree:

*Size*.—Large, usually pruned to 3 to 3.5 meters in height and width for economical harvesting of fruit, varies with different cultural practices.

*Vigor*.—Vigorous, tree growth of approximately 1.5 to 2 meters in height the first growing season. Varies with type and fertility of soil, climatic conditions and cultural practices.

*Form*.—Upright, usually pruned to vase shape.

*Branching habit*.—Upright, crotch angle approximately 45°, increases with heavy crop load.

*Productivity*.—Productive, thinning and spacing of fruit necessary for desired marketable size. Fruit set varies with climatic conditions during blooming period.

*Bearer*.—Regular, adequate fruit set 4 consecutive years. No alternate bearing observed.

*Fertility*.—Self-fertile, sets fruit under bag.

*Density*.—Medium dense, pruned to vase shape to allow sunlight to center of tree to enhance fruit color and health of fruit spurs.

*Hardiness*.—Hardy in all stone fruit growing areas of California. Tree grown in USDA Hardiness Zone 9. Winter chilling requirement approximately 450 hours at or below 45° F.

Trunk:

*Size*.—Medium to large. Average circumference 71.1 cm at 22.9 cm above ground on a 6 year old tree.

*Stocky*.—Medium stocky.

*Texture*.—Medium shaggy, becomes rougher with age.

*Color*.—Varies from 5Y 5/2 to 2.5Y 2/2.

Branches:

*Size*.—Medium to large. Average circumference 10.9 cm at 1.2 meters above ground. Crotch angle approximately 45°, increases with heavy crop load.

*Surface texture*.—New growth relatively smooth. Mature growth medium rough, becomes rougher with age.

*Lenticels*.—Size — medium. Average 35 in a 25.8 sq cm area of a branch. Average length 2.2 mm. Average width 1.0 mm. Color varies from 10YR 6/8 to 10YR 7/8.

*Color*.—New growth varies from 2.5GY 5/8 to 5GY 4/8. Old growth varies from 5YR 2/2 to 7.5YR 2/2, varies with age of growth.

Leaves:

*Size*.—Large. Average length 98.5 mm. Average width 89.1 mm.

*Form*.—Ovate.

*Apex*.—Cuspidate.

*Base*.—Cuneate.

*Margin*.—Serrate.

*Thickness*.—Medium.

*Surface texture*.—Upper surface relatively smooth, slightly indented over midrib and leaf veins, glabrous. Lower surface relatively smooth, small ridges created by midrib and pinnate venation, glabrous.

*Petiole*.—Average length 33.0 mm. Average width 1.7 mm. Color varies from 2.5GY 5/6 to 7.5R 3/4, color varies with exposure to sunlight. Longitudinally grooved. Surface — glabrous.

*Glands*.—Type — globose. Size — small. Average length 0.8 mm. Average diameter 0.6 mm. Number varies from 2 to 4, average number 3. Located primarily on upper portion of petiole and base of leaf blade. Color varies from 5GY 5/4 to 5GY 5/6.

*Stipules*.—Average length 8.1 mm. Average number — 2. Edges — pectinate. Color 2.5R 3/8.

*Color*.—Upper surface varies from 5GY 3/6 to 7.5GY 3/6. Lower surface varies from 5GY 5/4 to 5GY 4/4. Midvein color varies from 2.5GY 5/4 to 5GY 5/4.

Flower buds:

*Size*.—Large. Average length 14.2 mm. Average diameter 10.3 mm.

*Hardiness*.—Hardy with respect to California winters.

*Form*.—Conical, becoming slightly elongated before opening.

*Pedicel*.—Average length 1.7 mm. Average width 2.2 mm. Color varies from 10Y 6/8 to 2.5GY 6/6.

*Color*.—Varies from 5RP 7/8 to 7.5RP 9/2.

*Number of buds per spur*.—Average 12, varies from 7 to 17.

Flowers:

*Blooming period*.—Date of First Bloom Feb. 10, 2011. Date of Petal Fall Feb. 20, 2011, varies slightly with climatic conditions.

*Size*.—Medium. Average height 17.7 mm. Average diameter 27.2 mm.

*Petals*.—Normally 5, alternately arranged to sepals. Size — medium. Average length 14.7 mm. Average width 14.8 mm. Form — orbicular. Margin — sinuate. Color varies from 5RP 9/2 to 5RP 8/6, fades with age of flower.

*Sepals*.—Normally 5, alternately arranged to petals. Size — medium to large. Average length 9.0 mm. Average width 6.4 mm. Shape — triangular. Margin — entire. Both upper and lower surfaces glabrous. Color — upper surface 7.5R 2/8. Lower surface varies from 5R 2/8 to 7.5R 2/8.

*Stamens*.—Average 29 per flower. Average filament length 11.3 mm. Filament color N 9.5/(white). Anther color varies from 5Y 8/8 to 5Y 8/10.

*Pollen*.—Present. Self-fertile, sets fruit under bag. Color varies from 2.5Y 7/10 to 5Y 7/10.

*Pistil*.—Normally one. Average length 12.6 mm. Position of stigma average of 3.1 mm below anthers. Surface — pubescent. Color varies from 10Y 8.5/6 to 2.5GY 8/6.

*Fragrance*.—Slight fragrance.
*Color*.—Varies from 5RP 9/2 to 5RP 8/4, fades with age of flower.
*Number flowers per flower bud*.—Average 3, varies from 1 to 4.
*Pedicel*.—Average length 2.8 mm. Average width 2.4 mm. Color varies from 10Y 8.5/6 to 2.5GY 8/6.

Fruit:
*Maturity when described*.—Firm ripe.
*Date of first picking*.—May 10, 2011.
*Date of last picking*.—May 21, 2011, varies slightly with climatic conditions.
*Size*.—Large. Average diameter axially 59.1 mm. Average transversely in suture plane 56.6 mm. Average across suture plane 52.5 mm. Average weight 102.2 grams, varies slightly with fertility of soil, amount of thinning and climatic conditions.
*Form*.—Slightly elongated.
*Suture*.—Lipped.
*Ventral surface*.—Lipped.
*Apex*.—Retuse.
*Base*.—Retuse.
*Stem cavity*.—Rounded to slightly elongated in suture plane. Average depth 6.8 mm. Average diameter 8.5 mm.

Stem:
*Size*.—Small. Average length 8.8 mm. Average diameter 3.9 mm.
*Color*.—Varies from 5GY 5/6 to 5GY 4/6.

Flesh:
*Ripens*.—Evenly.
*Texture*.—Firm.
*Fibers*.—Few, small, tender.
*Firmness*.—Firm, comparable to commercial apricots.
*Aroma*.—Moderate.
*Amydgalin*.—Undetected.
*Eating quality*.—Good.
*Flavor*.—Good, good balance between acid and sugar.
*Juice*.—Moderate amount, enhances flavor.
*Brix*.—Average 13.2°, varies slightly with amount of fruit per tree and climatic conditions.
*Color*.—Varies from 7.5YR 7/10 to 7.5YR 7/12. Pit cavity varies from 7.5YR 7/10 to 7.5YR 6/12.

Skin:
*Thickness*.—Medium.
*Surface*.—Slightly waffled.
*Pubescence*.—Moderate pubescence, short in length.
*Tendency to crack*.—None.
*Color*.—Orange. Ground color 7.5YR 7/10. Overspread with 7.5R 4/10.
*Tenacity*.—Tenacious to flesh.
*Astringency*.—Slight to none.

Stone:
*Type*.—Freestone.
*Size*.—Large. Average length 30.7 mm. Average width 22.6 mm. Average thickness 13.8 mm.
*Form*.—Ovoid.
*Base*.—Flat.
*Apex*.—Round.
*Surface*.—Slightly pitted throughout, a shallow groove on each side of suture extending from base to apex.
*Sides*.—Unequal, one side extending further from suture plane.
*Ridges*.—Very narrow, a small ridge near groove on each side of suture. Extend from base to apex.
*Tendency to split*.—None.
*Color*.—Varies from 7.5YR 4/6 to 10YR 4/4 when dry.
*Pit cavity*.—Average length 31.3 mm. Average width 24.1 mm. Average depth 7.4 mm. Color varies from 7.5YR 7/10 to 7.5YR 6/12.

Kernel:
*Size*.—Large. Average length 20.1 mm. Average width 12.4 mm. Average depth 7.3 mm.
*Form*.—Ovoid.
*Viability*.—Viable, complete embryo development.
*Skin*.—Color varies from N 9.5/(white) to 7.5Y 9/2.

Use:
*Dessert*.—Market — local and long distance.

Keeping quality: Good, held firm in cold storage 14 days at 38° to 42° F. without shriveling, internal breakdown of flesh or appreciable loss of eating quality.

Shipping quality: Good, showed minimal flesh bruising or skin scarring during picking, packing and shipping trials.

Plant fruit resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct interspecific tree, substantially as illustrated and described.

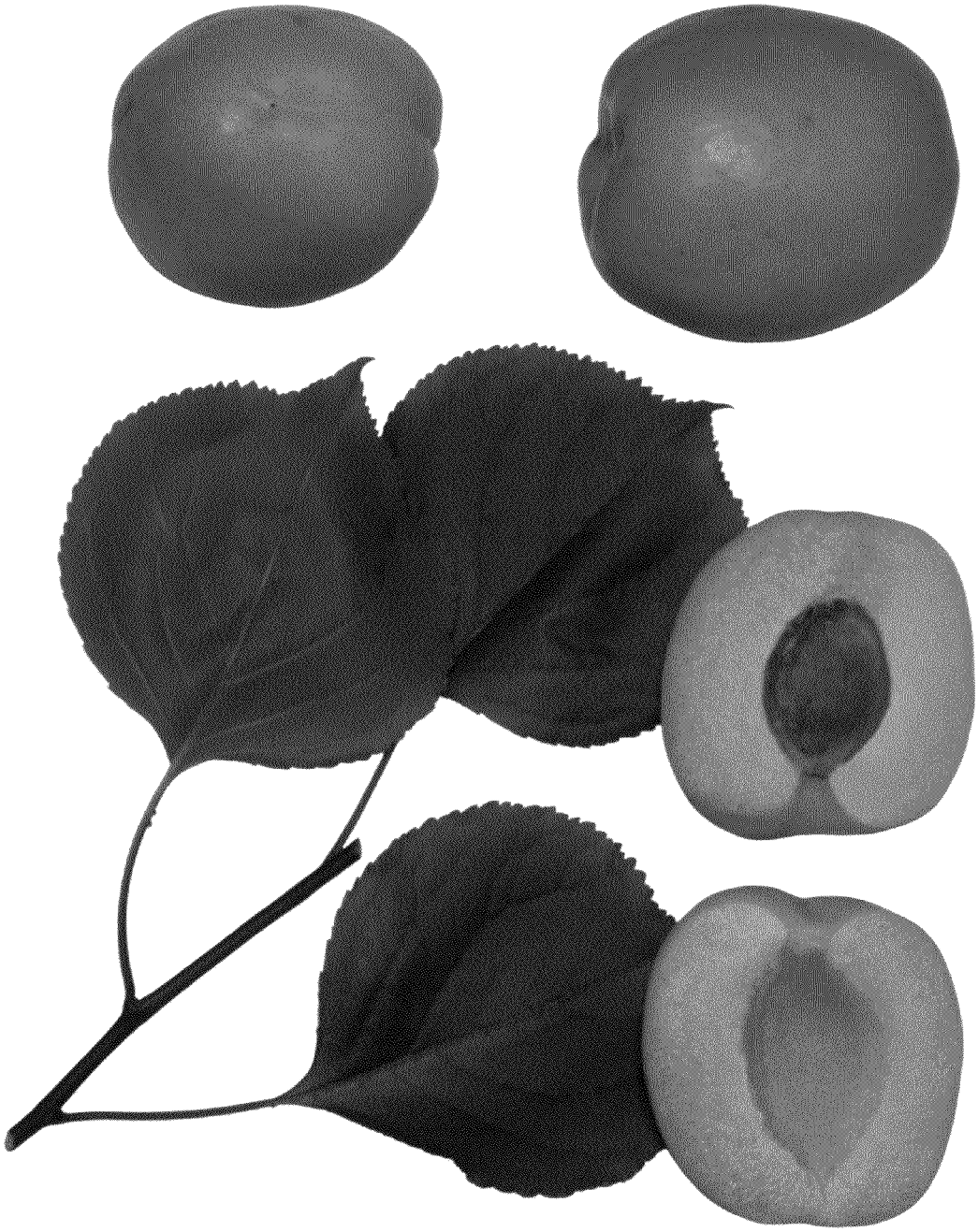

* * * * *